United States Patent [19]

Szantay et al.

[11] 4,057,551
[45] Nov. 8, 1977

[54] INDOLO[2,3-A]QUINOLIZINES

[75] Inventors: Csaba Szantay; Lajos Szabo; Gyorgy Kalaus; Egon Karpati; Laszlo Szporny, all of Budapest, Hungary

[73] Assignee: Richter Gedeon Vegyeszeti Gyar Rt., Budapest, Hungary

[21] Appl. No.: 614,240

[22] Filed: Sept. 17, 1975

[30] Foreign Application Priority Data

Sept. 27, 1974 Hungary .................................. RI 545

[51] Int. Cl.$^2$ .................. C07D 471/02; C07D 455/02
[52] U.S. Cl. .......................... 260/293.55; 260/293.53; 260/294.9; 424/267
[58] Field of Search ....................... 260/293.53, 293.55

[56] References Cited
U.S. PATENT DOCUMENTS

| 3,478,051 | 11/1969 | Houlihan et al. | 260/293.55 |
| 3,536,725 | 10/1970 | Schut | 260/294.9 |
| 3,799,933 | 3/1974 | Le Men et al. | 260/293.53 |

OTHER PUBLICATIONS

Szantay et al., Tetrahedron Letters 11, 1405-1407 (1968).

Primary Examiner—John M. Ford
Attorney, Agent, or Firm—Toren, McGeady and Stanger

[57] ABSTRACT

New compounds of the general formula (I)

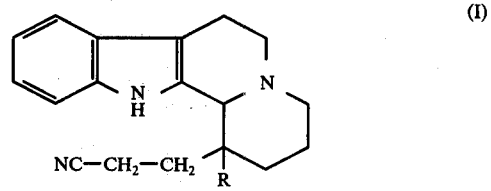

wherein R stands for an alkyl group, have been prepared by reducing a compound of the general formula (II)

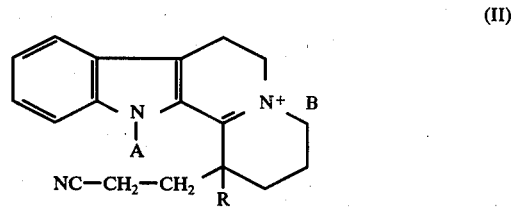

wherein R stands for alkyl, B stands for $H_2O$ or an $X^-$ anion derived from an acid, and if B is an $X^-$ anion, A represents hydrogen, whereas if B is $H_2O$, A represents an electron pair. If desired, the racemic compounds of the general formula (I) can be resolved to yield the corresponding optically active isomers. The free bases of the general formula (I) can be converted into their pharmaceutically acceptable salts, or the salts can be treated with an alkaline agent to yield the free bases.

The compounds of the general formula (I) can be used in the therapy primarily as vasodilatating agents.

5 Claims, No Drawings

INDOLO[2,3-a]QUINOLIZINES

This invention relates to new indolo-quinolizidine derivatives and pharmaceutical compositions containing the same, as well as to a process for the preparation thereof.

More particularly, the invention relates to new indolo-quinolizidine derivatives of the general formula (I) or salts or optically active isomers thereof

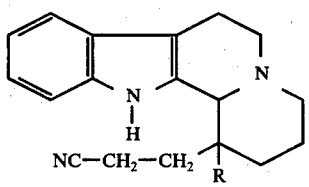

(I)

wherein R stands for an alkyl group.

Some of the 1,1-disubstituted indolo-quinolizidine compounds, such as vincamine and its derivatives, are known to possess valuable therapeutical effects. The preparation of these known indolo-quinolizidines was described by E. Wenkart et al. (J. Am. Chem. Soc. 87, 1580/1956/), and by Szantay et al. (Tetrahedron Letters 1973, 191).

1,1-Disubstituted indolo-quinolizines, containing an alkyl group and a cyanoethyl group in position 1 have, however, not been described so far.

In the compounds of the general formula (I) R represents a straight-chained or branched alkyl group, preferably a lower alkyl group with 1 to 6 carbon atoms. Of these groups e.g. the methyl, ethyl, n-propyl, isopropyl, n-butyl, isobutyl, tert-butyl, n-amyl, isoamyl and hexyl groups are to be mentioned. Particularly preferred are those compounds of the general formula (I) in which R stands for ethyl or n-butyl.

The new compounds of the general formula (I), or their salts or optically active isomers, respectively, are prepared according to the invention as follows:

A compound of the general formula (II),

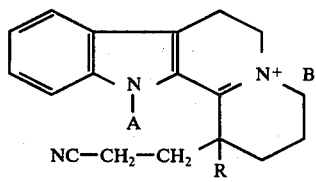

(II)

wherein R stands for alkyl, B stands for $H_2O$ or an $X^-$ anion derived from an acid, and if B is an $X^-$ anion, A represents hydrogen, whereas if B is $H_2O$, A represents an electron pair, is reduced, and, if desired, a compound of the general formula (I), wherein R has the same meaning as defined above, is reacted with an acid, or, if desired, a salt of a compound of the general formula (I), wherein R has the same meaning as defined above, is treated with a base, and/or, if desired, a racemic compound of the general formula (I), wherein R has the same meaning as defined above, or a salt thereof is resolved to obtain the respective optically active substances.

This process is highly stereospecific and leads to the formation of only one of the two possible stereoisomers. The above process yields only such compounds of the general formula (I) in which the 1-alkyl group and the 12b-hydrogen atom are in trans arrangement.

The compounds of the general formula (II), used as starting substances in the process of the invention, are also new. These compounds can be prepared by reacting a compound of the general formula (III),

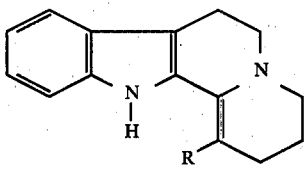

(III)

wherein R has the same meaning as defined above, with acrylonitrile.

In the process of the invention both sub-groups of the compounds having the general formula (II), i.e. both the compounds of the general formula (IIa)

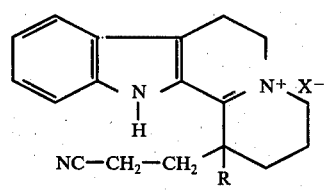

(IIa)

and the compounds of the general formula (IIb),

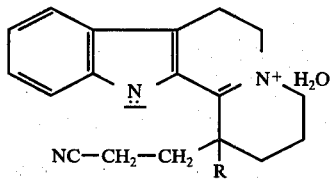

(IIb)

wherein R and $X^-$ each have the same meanings as defined above, can be used as starting substances.

Any reducing agent capable of saturating an endocyclic double bond without hydrogenating simultaneously the cyano group can be used in accordance with the process of the invention. The reduction is performed preferably with a chemical reducing agent or by catalytic hydrogenation.

In chemical reduction, preferably a complex metal hydride, particularly a borohydride, such as lithium or sodium borohydride, or formic acid is used as reducing agent.

Of the complex metal hydrides the borohydrides are particularly preferred, because of their outstanding selectivity. When a borohydride is used as reducing agent, the reaction is performed in a solvent or suspending agent which is inert towards the reaction. One may use to advantage an aliphatic alcohol, such as methanol, or an aqueous alcohol, such as aqueous methanol.

The borohydride is added to the reaction mixture in excess, preferably in an amount of 3 to 10 moles, particularly about 6 moles per one mole of the starting substance. The reaction time and temperature are not critical, and their optimum values depend primarily on the reactivity of the starting substance used. The reaction is performed generally at about 0° C, by stirring the reaction mixture for about 30 minutes to about 3 hours.

According to a preferred method of the invention a compound of the general formula (IIa) or (IIb), wherein R and $X^-$ each have the same meanings as defined above, is suspended in an inert solvent, preferably in an aliphatic alcohol, the suspension is cooled to about 0° C, and the borohydride (preferably sodium borohydride) is added to the suspension in small portions at the same temperatures.

The reaction mixture can be processed by methods known per se, e.g. by acidifying and concentrating the reaction mixture, dissolving the residue in water, rendering the solution alkaline, extracting the alkaline mixture, and evaporating the extract to dryness.

As mentioned above, formic acid can also be used as chemical reducing agent. Formic acid is added to the reaction mixture preferably as a substantially pure chemical (purity grade: 98 to 100%) in excess, preferably in an amount of 2 to 4 moles, particularly about 3 moles per one mole of the starting substance. The excess of formic acid also serves as a solvent medium for the reaction. The reaction is performed at elevated temperatures, preferably at bath temperatures of 80° to 120° C, particularly at bath temperatures of 95° to 100° C. The reaction time usually ranges from 10 to 30 hours. It is preferable to heat the mixture for about 20 hours. The reaction is perfomed preferably under an inert gas, such as nitrogen or argon. The reaction mixture is processed in a known way, e.g. by diluting the mixture with water, rendering it alkaline, extracting the aqueous-alkaline solution, and separating the product from the extract.

If catalytically activated hydrogen is used as reducting agent, preferably a metal belonging to the subgroups of the Periodic System, such as palladium, platinum, nickel, iron, copper, cobalt, chromium, zinc, molybdenum, tungsten, etc. or an oxide or sulfide thereof is used as hydrogenating catalyst.

The catalysts to be used in the process of the invention can be prepared e.g. by reducing their stable oxides with hydrogen directly in the reaction vessel. This method can be used e.g. when finely divided palladium or platinum is to be applied as hydrogenating catalyst. Alternatively, catalysts prepared by acidic or alkaline leaching of one metal from a binary alloy, such as Raney-nickel, can be used as well. The catalytic hydrogenation can also be performed in the presence of a supported catalyst; this enables to decrease considerably the amount of the expensive noble metals necessary for the reduction. Of the supports e.g. carbon (particularly charcoal), silicium dioxide, aluminium oxide, and the sulfates and carbonates of alkaline earth metals are to be mentioned.

When the reduction is performed with catalytically activated hydrogen, one employs preferably palladium (particularly palladium-on-charcoal) or Raney-nickel as catalyst. The catalysts are always selected in accordance with the reaction conditions and the characteristics of the substance to be hydrogenated.

The catalytic reduction is performed in a solvent inert towards the reaction, such as an alcohol, ethyl acetate, glacial acetic acid, etc., or a mixture of such solvents. The aliphatic alcohols, such as methanol and ethanol, proved to be the most preferred solvents. If platinum oxide is used as catalyst, the reaction is performed preferably in a neutral or slightly acidic medium, whereas if Raney-nickel is applied, the reaction is conducted preferably in a neutral or alkaline medium.

The temperature, pressure and time of the catalytic reduction may vary within wide limits depending on the starting substances. It is preferable, however, to conduct the reaction at room temperature and under atmospheric pressure until the cessation of the hydrogen uptake. The hydrogen uptake ceases generally within 10 minutes to 5 hours.

The reaction mixture is processed in a manner known per se, e.g. by filtering the mixture and evaporating the filtrate to dryness.

The catalytic hydrogenation is performed preferably as follows: a catalyst (preferably palladium-on-charcoal) is washed with a mixture of water and the solvent used in the hydrogenation process (preferably methanol), and the washed catalyst is prehydrogenated. Thereafter a solution of the appropriate starting substance of the general formula (IIa) or (IIb) in the above solvent is added to the pre-treated catalyst, and the resulting mixture is hydrogenated, preferably at room temperature and under atmospheric pressure, until the hydrogen uptake ceases.

The product is generally separated from the reaction mixture as a crystalline solid. If, however, an amorphous powder or an oily substance is obtained, it can usually be crystallized very easily from a suitable solvent, such as an aliphatic alcohol, e.g. methanol, etc.

The free bases of the general formula (I) can be converted into their acid addition salts. For this purpose preferably pharmaceutically acceptable mineral or organic acids, such as hydrogen halides (e.g. hydrochloric acid, hydrobromic acid, etc.), phosphoric acid, organic carboxylic acids (e.g. acetic acid, propionic acid, glycolic acid, maleic acid, succinic acid, tartaric acid, citric acid, salicyclic acid, benzoic acid, etc.), alkylsulfonic acids (e.g. methanesulfonic acid), arylsulfonic acids (e.g. p-toluenesulfonic acid) etc. can be used. In turn, the acid addition salts can be treated with a base to yield the compounds of the general formula (I) in the form of the free bases.

The salt formation is performed preferably in an inert solvent, particularly in an aliphatic alcohol, such as methanol. The base of the general formula (I) is dissolved in the solvent, and the mixture is acidified slightly (to about pH = 6) with the appropriate acid. The acid is added preferably in small portions. Thereafter the separated salt of the starting base is isolated from the reaction mixture.

The compounds of the general formula (I) contain an asymmetric carbon atom, they may exist therefore in the form of optically active isomers. The synthesis according to the invention yields racemic end-products, which can be resolved into the individual optically active isomers by known methods.

The process of the invention enables to produce the compounds of the general formula (I) with hith yields and in forms easy to identify. The analytical data of the obtained compounds are in good agreement with the calculated values. The structures of the obtained products can be confirmed further by IR and NMR spectroscopy.

The compounds of the general formula (I) and their pharmaceutically acceptable acid addition salts possess valuable biological properties. According to the results of the tests carried out on narcotized dogs, the compounds possess significant vasodilatating effects. The compounds increase primarily the cerebral blood flow, but some of them effectively increase the blood flow of the limbs as well. In comparison with the significant increase of the blood flow, the temporary drop in blood pressure (lasting from about 1 to 2 minutes) and the increase of heart rate are relatively small.

The tests were performed on dogs narcotized with chloralose-urethane. The blood flow of the limbs was measured at the arteria femoralis, whereas the cerebral blood flow was investigated by measuring the flow of the arteria carotis interna. The circulation resistance was calculated from the blood pressure and blood flow values.

The compounds under examination were administered in intravenous dosages of 1 mg./kg. The observed changes were expressed as percentages in relation to the controls. 6 animals were used in each of the tests, and the data of Table 1 are the mean values calculated for these groups.

For comparison purposes the respective data of apovincaminic acid ethyl ester, the most active one of the compounds with related structures (see Hungarian Pat. No. 163,434) are also given.

Table 1

| Substance | (1) | (2) | (3) | (4) | (5) | (6) |
|---|---|---|---|---|---|---|
| (A) | +58 | −35 | +16 | −20 | −28 | +14 |
| (B) | +53.8 | −38.4 | +56.2 | −44.4 | −43.5 | +43.5 |
| (C) | +76.8 | −49.5 | +44.9 | −30.2 | −11.1 | +33.1 |

Notes:
(1) blood flow of the limbs
(2) circulation resistance of the limb blood vessels
(3) cerebral blood flow
(4) circulation resistance of the cerebral blood vessels
(5) blood pressure
(6) heart rate
(A) apovincaminic acid ethyl ester (reference substance)
(B) 1α-ethyl-1β-(2-cyanoethyl)-1,2,3,4,6,7,12,12bβ-octahydroindolo(2,3-a)quinolizine
(C) 1α-n-butyl-1β-(2-cyanoethyl)-1,2,3,4,6,7,12,12bβ-octahydroindolo(2,3-a)quinolizine As appears from the data of the Table, the new compounds according to the invention are about 1.5 times as active as the reference substance with respect to the increase of the blood flow in the limbs, whereas their activities exceed more than 3 times that of the reference substance with respect to the increase of the cerebral blood flow.

The effective intravenous or oral dosage of the new compounds may vary within about 0.1 to 2 mg./kg. body weight. It should be noted, however, that the actual dosage is always determined in accordance with the needs of the patient, thus in some instances dosages lower or higher than those mentioned above are to be applied.

The compounds of the general formula (I) or the pharmaceutically acceptable acid addition salts thereof can be converted into pharmaceutical compositions suitable for enteral or parenteral administration. These compositions may contain the new compounds according to the invention either alone or in combination with other biologically active substances. When preparing the pharmaceutical compositions the active agent(s) is(are) admixed with conventional inert, non-toxic, pharmaceutically acceptable carriers and/or diluents. As carrier e.g. water, gelatine, lactose, starch, magnesium stearate, talc, vegetable oils, gum arabic, polyalkylene glycols, vaseline, etc. can be used. The amount of the solid carrier may vary within wide limits; the dosage units may contain e.g. 25 to 1000 mg. of solid carrier. The compositions may optionally contain conventional pharmaceutical auxiliary agents, such as preservatives, salts for adjusting the osmotic pressure, buffers, flavouring agents, etc. The pharmaceutical compositions can be prepared in conventional forms, e.g. as solid formulations (tablets, coated tablets, capsules, etc.) or as liquid preparations (e.g. solutions, suspensions, emulsions, etc.). The obtained compositions can be sterilized, or subjected to other finishing operations, if necessary.

The invention is elucidated in detail by the aid of the following non-limiting Examples.

EXAMPLE 1

1α-Ethyl-1β-(2-cyanoethyl)-1,2,3,4,6,7,12,12bβ-octahydro-indolo(2,3-a)quinolizine a. 1 g. of an 5% palladium-on-carbon catalyst is washed thoroughly with distilled water and methanol, thereafter it is suspended in a small amount of methanol, and the suspension is prehydrogenated. When the hydrogen uptake ceases, a solution of 1.50 g. (4.64 mmoles) of (1-ethyl-1,2,3,4,6,7-hexahydro-12H-indolo[2,3-a]quinolizin-1-yl)-propylnitrile in 150 ml. of methanol is added to the suspension, and the mixture is hydrogenated at room temperature and under atmospheric pressure. After the uptake of the theoretical amount (110 ml.) of hydrogen, which requires about 15 minutes, the catalyst is filtered off, washed with methanol, and the liquids are evaporated in vacuo. The obtained 1.35 g. of solid residue are recrystallized from twentyfold amount of methanol to obtain 1.20 g. (84.8%) of 1α-ethyl-1β-(2-cyanoethyl)-1,2,3,4,6,7,12,12bβ-octahydroindolo(2,3-a)quinolizine as a yellow, crystalline substance melting at 228°–229° C.

Analysis:
calculated for $C_{20}H_{25}N_3$ (M = 307.42): C: 78.13% H: 8.20% N: 13.67% found: C: 78.36% H: 8.39% N: 13.38%

IR-spectrum (in KBr pellet): 3370 (ind.=NH) and 2248 (—CN) cm$^{-1}$.

NMR-spectrum (in deuterochloroform): 2.09 (1H, ind.=NH), 2.38–2.91 (4H, aromatic protons), 6.58 (1H, proton of the anellated ring system) and 9.13 (3H, —CH$_3$) ppm.

b. 1.50 g. (4.64 mmoles) of (1-ethyl-1,2,3,4,6,7-hexahydro-12H-indolo[2,3-a]quinolizin-1-yl)-propionitrile are suspended in 100 ml. of methanol, the suspension is cooled to 0° C, and 1.0 g. (26.5 mmoles) of sodium borohydride are added to the stirred suspension in small portions at the same temperature. After the addition the mixture is stirred for one hour, thereafter it is acidified to pH = 3 with 5 n hydrochloric acid. The reaction mixture is evaporated in vacuo to a final volume of 10 ml. This suspension is diluted with distilled water, and rendered strongly alkaline (pH∼10 to 11) with 40% aqueous sodium hydroxide solution under cooling. The alkaline mixture is extracted once with 20 ml. and twice with 10 ml. of dichloroethane. The organic solutions are combined, dried over magnesium sulfate, filtered, and the filtrate is evaporated in vacuo. The obtained solid residue is recrystallized from methanol to obtain 1.20 g. (84.8%) of a yellow, crystalline powder melting at 228°–229° C. The obtained compound is identical with the substance prepared according to paragraph a).

c. 12.0 g. (37.2 mmoles) of (1-ethyl-1,2,3,4,6,7-hexahydro-indolo[2,3-a]quinolizin-1-yl)-propionitrile are dissolved in 4.75 ml. (5.78 g., 125 mmoles) of 98–100% formic acid, and the solution is maintained on a hot (95° to 100° C) water bath under argon atmosphere for 20 hours. When the reaction terminates the acidic solution is diluted with 50 ml. of distilled water, and alkalinized to about pH 10 to 11 with 40% aqueous sodium hydroxide solution under cooling. The alkaline solution is extracted with 50 ml., 30 ml. and 20 ml. of dichloroethane. The organic solutions are combined, dried over magnesium sulfate, filtered, and the filtrate is evaporated in vacuo. The solid residue is recrystallized from methanol.

9.05 g (79.2%) of 1α-ethyl-1β-(2-cyanoethyl)-1,2,3,4,6,7,12,12bβ-octahydro-indolo(2,3-a)quinolizine are obtained as a crystalline substance melting at 227°–229° C. This substance is identical with the product obtained as described in paragraph a).

EXAMPLE 2

1α-n-Butyl-1β-(2-cyanoethyl)-1,2,3,4,6,7,12,12bβ-octahydro-indolo(2,3-a)quinolizine a. 0.8 g. of an 5% palladium-on-carbon catalyst is washed thoroughly with distilled water and methanol, thereafter it is suspended in about 20 ml. of methanol, and the suspension is prehydrogenated. When the hydrogen uptake ceases, a solution of 0.75 g. (1.73 mmoles) of 1-n-butyl--(2-cyanoethyl)-1,2,3,4,6,7-hexahydro-12H-indolo(2,3-a)quinolizinium perchlorate in 600 ml. of methanol is added to the suspension, and the mixture is hydrogenated at room temperature and under atmospheric pressure. After the uptake of the theoretical amount of hydrogen, which requires about 2 hours, i.e. when the hydrogen uptake ceases, the catalyst is filtered off, and the filtrate is evaporated in vacuo. The obtained solid residue is recrystallized from 2 ml. of methanol. 6.60 g. (79.6%) of 1α-n-butyl-1β-(2-cyanoethyl)-1,2,3,4,6,7,12,12bβ-octahydroindolo(2,3-a)quinolizinium percholorate are obtained; m.p.: 227°–229° C under decomposition.

b. 2.15 g. (5.97 mmoles) of 1-n-butyl-1-(2-cyanoethyl)-1,2,3,4,6,7-hexahydro-12H-indolo(2,3-a)quinolizinium perchlorate are suspended in 750 ml. of methanol, the suspension is cooled to 0° C, and 1.50 g. (39.6 mmoles) of sodium borohydride are added to the stirred suspension in small portions at the same temperature. After the addition the mixture is stirred for one hour, thereafter it is acidified to pH = 3 with 5 n hydrochloric acid. The reaction mixture is evaporated in vacuo to a final volume of 10 ml., this concentration is diluted with 200 ml. of distilled water, and alkalinized to about pH 10 to 11 with 40% aqueous sodium hydroxide solution under ice cooling. The alkaline solution is extracted with 50 ml., 30 ml. and 20 ml. of dichloroethane. The organic solutions are combined, dried over magnesium sulfate, filtered, and the filtrate is evaporated in vacuo. The obtained oily residue is crystallized from twofold volume of ethanol. 0.95 g. (57.1 %) of 1α-n-butyl-1β-(2-cyanoethyl)-1,2,3,4,6,7,12,12bβ-octahydro-indolo(2,3-a)quinolizine are obtained as a white, crystalline substance melting at 188°–189° C.

Analysis:
calculated for $C_{22}H_{29}N_3$ (M = 335.48):
C: 78.76% H: 8.71% N: 12.53% found: C: 78.98% H: 8.72% N: 12.34%

IR-spectrum (in KBr pellet): 3395 (ind.=NH) and 2310 (—CN) cm$^{-1}$.

NMR-spectrum (in deuterochloroform): 1.97 (1H, ind.=NH), 2.42–2.98 (4H, aromatic protons) and 9.12 (3H, —CH$_3$) ppm.

EXAMPLE 3

(1-Ethyl-1,2,3,4,6,7-hexahydro-12H-indolo[2,3-a]quinolizin-1yl)-propionitrile (starting substance)

10.0 g (28.5 mmoles) of 1-ethyl-2,3,4,6,7,12-hexahydro-indolo(2,3-a)quinolizinium perchlorate are dissolved in 100 ml. of dichloromethane, and 75 ml. of distilled water and 20 ml. of a 2 n aqueous sodium hydroxide solution are added to the stirred soltion under argon atmosphere. The reaction mixture is stirred for 10 minutes, thereafter the separated organic phase is isolated and dried over anhydrous potassium carbonate. The drying agent is filtered off, 10 ml. of freshly distilled acrylonitrile are added to the filtrate, the mixture is flushed with argon, and it is allowed to stand at room temperature. The colour of the mixture turns deeper. After 2 days of standing the mixture is evaporated in vacuo at a bath temperature of maximum 40° to 50° C under argon atmosphere, and the dark red, oily residue is triturated with 5 ml. of methanol. The obtained orange red crystals, weighing 8.10 g., are filtered off, and recrystallized from 15-fold volume of methanol. 7.30 g. (79.4%) of (1-ethyl-1,2,3,4,6,7-hexahydro-12H-indolo[2,3-a]quinolizin-1-yl)-propionitrile are obtained: m.p.: 122°–123° C.

IR-spectrum (in KBr pellet): 2280 (—CN), 1662 and 1608 (=C=N$^+$=) cm$^{-1}$.

EXAMPLE 4

1-Ethyl-1-(2-cyanoethyl)-1,2,3,4,6,7-hexahydro-12H-indolo(2,3-a)quinolizinium perchlorate (starting substance)

1 g. of (1-ethyl-1,2,3,4,6,7-hexahydro-12H-indolo[2,3-a]quinolizin-1-yl)-propionitrile is dissolved in 20 ml. of hot methanol, and the solution is acified to pH = 6 with 70% perchloric acid. The separated yellow crystals are filtered off and dried. 1.05 g. of a crude product, melting at 209°–211° C, are obtained. After recrystallization from methanol, the obtained 1-ethyl-1-(2-cyanoethyl)-1,2,3,4,6,7-hexahydro12H-indolo(2,3-a)quinolizinium perchlorate melts at 211°–212° C.

Analysis:
calculated for $C_{20}H_{24}N_3ClO_4$ (M = 405.86):
C: 59.18% H: 5.96% N: 10.35% found: C: 59.23% H: 6.02% N: 10.49%

IR-spectrum (in KBr pellet): 3290 (ind.=NH), 2360 (—CN) and 1620 (=C=N$^+$=) cm$^{-1}$.

EXAMPLE 5

1-n-Butyl-1-(2-cyanoethyl)-1,2,3,4,6,7-hexahydro-12H-indolo(2,3-a)quinolizinium perchlorate (starting substance)

5.0 g. (13.3 mmoles) of 1-n-butyl-2,3,4,6,7,12-hexahydro-indolo(2,3-a)quinolizinium perchlorate are suspended in 50 ml. of dichloromethane, and 50 ml. of distilled water and 10 ml. of a 2 n aqueous sodium hydroxide solution are added to the stirred solution under argon atmosphere. The reaction mixture is stirred for 10 minutes, thereafter the organic phase is separated, and dried over anhydrous potassium carbonate. The drying agent is filtered off, 5.0 ml. of freshly distilled acrylonitrile are added to the filtrate, the mixture is flushed with argon, and allowed to stand at room temperature. After 3 days of standing the mixture is evaporated in vacuo. The red, oily residue is dissolved in 5 ml. of methanol, and the solution is acidified to pH = 6 with 70% perchloric acid. The separation of crystals is initiated by scraping the wall of the flask, and then the flask is put into a refrigerator.

The separated yellow crystals are filtered off and washed with cold methanol. The obtained 4.20 g. of crystalline substance (m.p.: 215°–220° C) is recrystallized from fivefold volume of methanol. 3.70 g. (64.1%) of 1-n-butyl-1-(2-cyanoethyl)-1,2,3,4,6,7-hexahydro-12H-indolo(2,3-a)quinolizinium perchlorate are obtained in the form of yellow needles melting at 224°–226° C.

Analysis:
calculated for $C_{22}H_{28}N_3ClO_4$ (M = 433.91):

C: 60.87% H: 6.50% N: 9.68% found: C: 6.60% H: 6.29% N: 9.82%

IR-spectrum (in KBr pellet): 3328 (ind.=NH), 2304 (—CN), 1625 and 1605 (=C=N+=) cm$^{-1}$.

What we claimed is:
1. A compound of the formula (I),

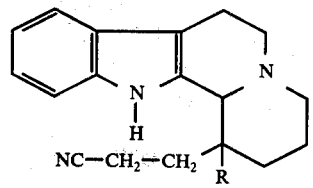

wherein R is an alkyl group having 1 to 6 carbon atoms, and a pharmaceutically acceptable salt thereof.

2. 1α-Ethyl-1β-(2-cyanoethyl)-1,2,3,4,6,7,12,12bβ-octahydro-indolo(2,3-a)quinolizine.

3. 1α-n-Butyl-1β-(2-cyanoethyl)-1,2,3,4,6,7,12,12bβ-octahydro-indolo(2,3-a)quinolizine.

4. 1α-Ethyl-1β-(2-cyanoethyl)-1,2,3,4,6,7,12,12bβ-octahydro-indolo(2,3-a)quinolizinium perchlorate.

5. 1α-n-Butyl-1β-(2-cyanoethyl)-1,2,3,4,6,7,12,12bβ-octahydro-indolo(2,3-a)quinolizinium perchlorate.

* * * * *